United States Patent [19]

Waltuck et al.

[11] Patent Number: 5,026,151
[45] Date of Patent: Jun. 25, 1991

[54] VISUAL FUNCTION TESTER WITH BINOCULAR VISION TESTING

[75] Inventors: Morey H. Waltuck, Sharon; Robert N. McKnight, Andover; Eliezer Peli, Newton, all of Mass.

[73] Assignee: Mentor O & O, Inc., Norwell, Mass.

[21] Appl. No.: 370,630

[22] Filed: Jun. 23, 1989

[51] Int. Cl.⁵ .......................... A61B 3/02; A61B 3/08
[52] U.S. Cl. ................................. 351/246; 351/243; 351/201
[58] Field of Search ............... 351/237, 238, 240, 243, 351/246, 201, 202; 350/132; 358/92

[56] References Cited

U.S. PATENT DOCUMENTS

| | | |
|---|---|---|
| 3,554,203 | 12/1970 | Garcia . |
| 3,609,016 | 9/1971 | Iampolsky . |
| 3,639,042 | 2/1972 | Grolman ........................... 351/30 |
| 3,969,020 | 7/1976 | Lynn et al. . |
| 4,015,899 | 4/1977 | Humphrey . |
| 4,239,351 | 12/1980 | Williams et al. .................... 351/36 |
| 4,385,806 | 5/1983 | Fergason ....................... 350/347 R |
| 4,411,501 | 10/1983 | Tagnon ............................ 351/202 |
| 4,418,993 | 12/1983 | Lipton ............................... 352/57 |
| 4,424,529 | 1/1984 | Roese et al. ....................... 358/88 |
| 4,436,376 | 3/1984 | Fergason ........................... 350/332 |
| 4,472,037 | 9/1984 | Lipton .............................. 352/57 |
| 4,523,226 | 6/1985 | Lipton et al. ....................... 358/88 |
| 4,536,065 | 8/1985 | Sheingorn ......................... 351/239 |
| 4,540,243 | 9/1985 | Fergason ........................... 350/337 |
| 4,562,463 | 12/1985 | Lipton et al. ....................... 358/88 |
| 4,567,513 | 1/1986 | Imsand ............................ 358/92 |
| 4,583,117 | 4/1986 | Lipton et al. ....................... 358/88 |
| 4,672,434 | 6/1987 | Suzuki et al. ...................... 358/88 |
| 4,698,668 | 10/1987 | Milgram ........................... 358/92 |
| 4,722,943 | 9/1988 | Nakagawa et al. .................. 358/92 |
| 4,723,159 | 2/1988 | Imsand ............................ 358/88 |
| 4,726,673 | 2/1988 | Blankehorn ....................... 351/238 |
| 4,736,246 | 4/1988 | Nishikawa ......................... 358/88 |
| 4,870,486 | 9/1989 | Nakagawa et al. ............. 350/132 X |

Primary Examiner—Rodney B. Bovernick
Attorney, Agent, or Firm—Herbert F. Schwartz; Richard A. Inz; Gerard A. deBlasi

[57] ABSTRACT

A visual function tester with binocular vision testing capabilities is disclosed, which includes a video display monitor and optical means, such as stereo vision glasses, to control the patient's viewing of the display. The opening and closing of the apertures of the glasses is synchronized to the display of a variety of visual acuity images. Certain images are made visible to each eye but not visible to the other, and certain images are displayed such that they appear out of the plane of the images. Methods for use of the apparatus are also disclosed.

14 Claims, 12 Drawing Sheets

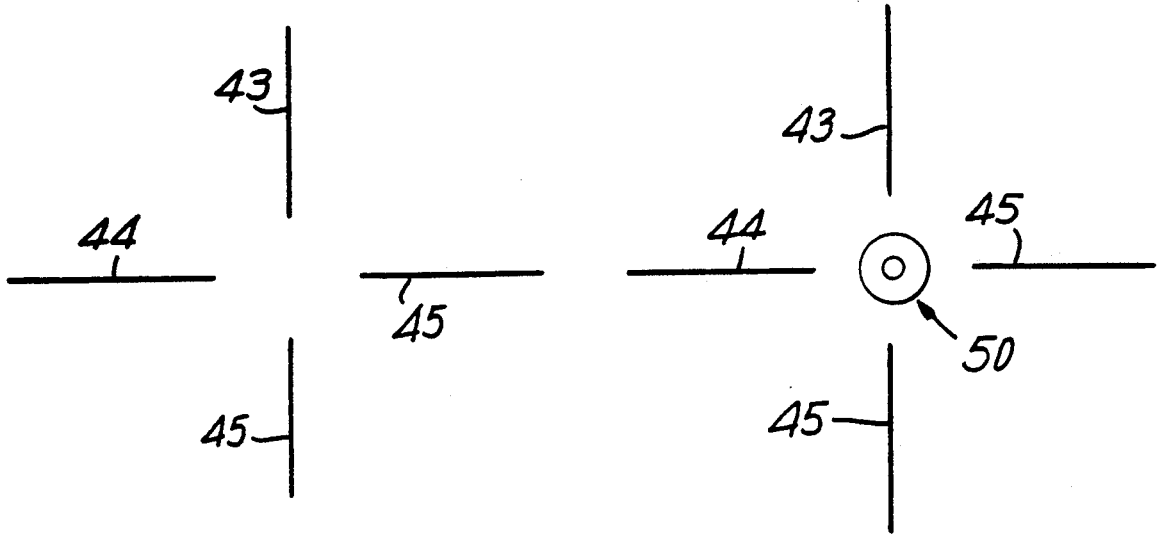
FIG. 5a   FIG. 5b
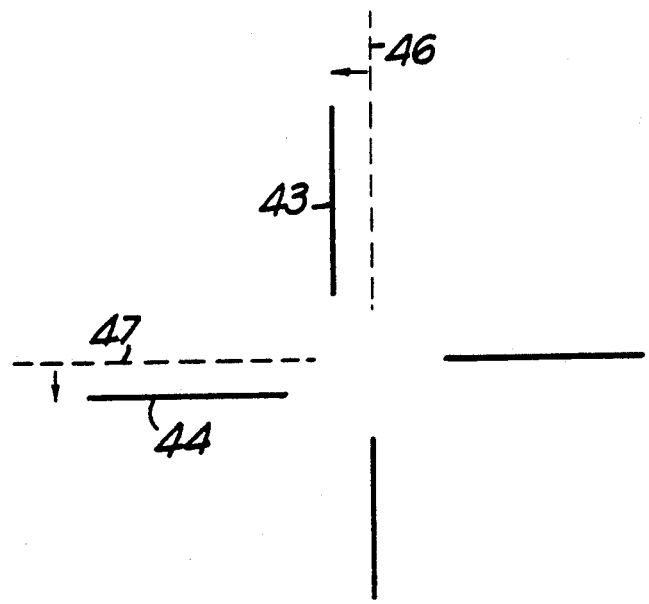
FIG. 6

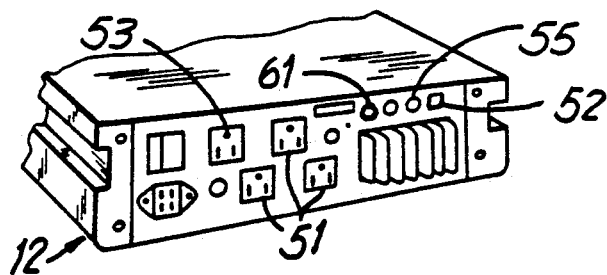
FIG. 11
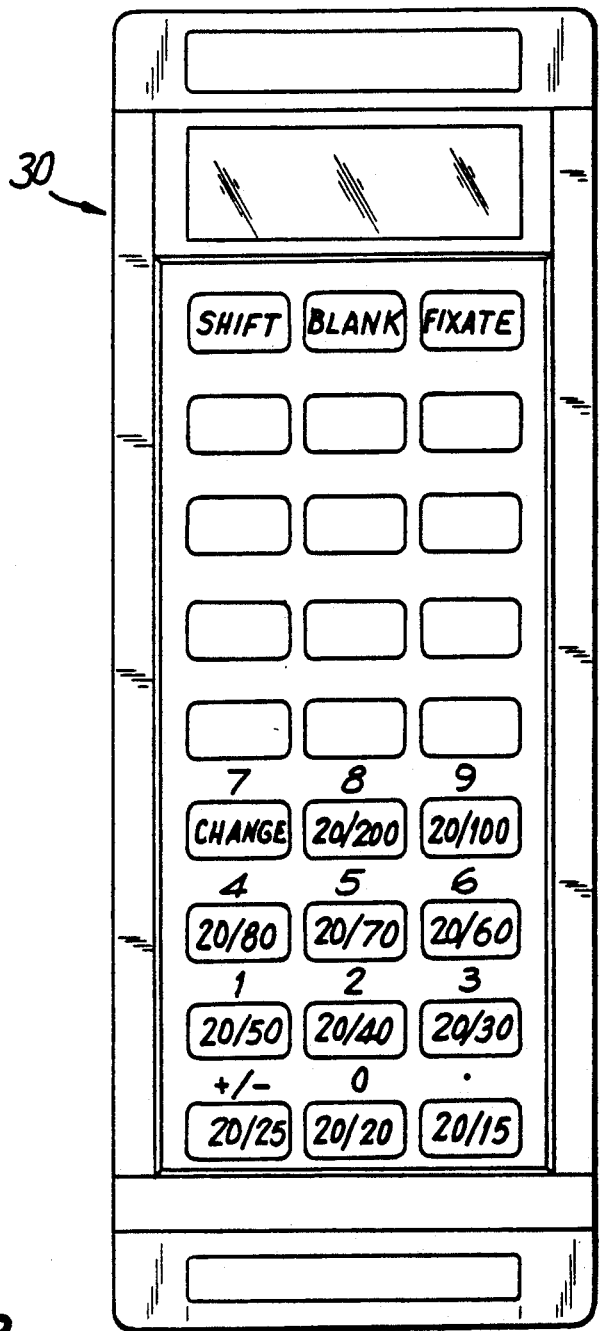
FIG. 12
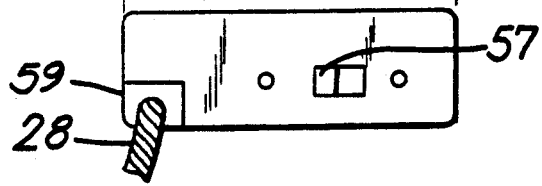

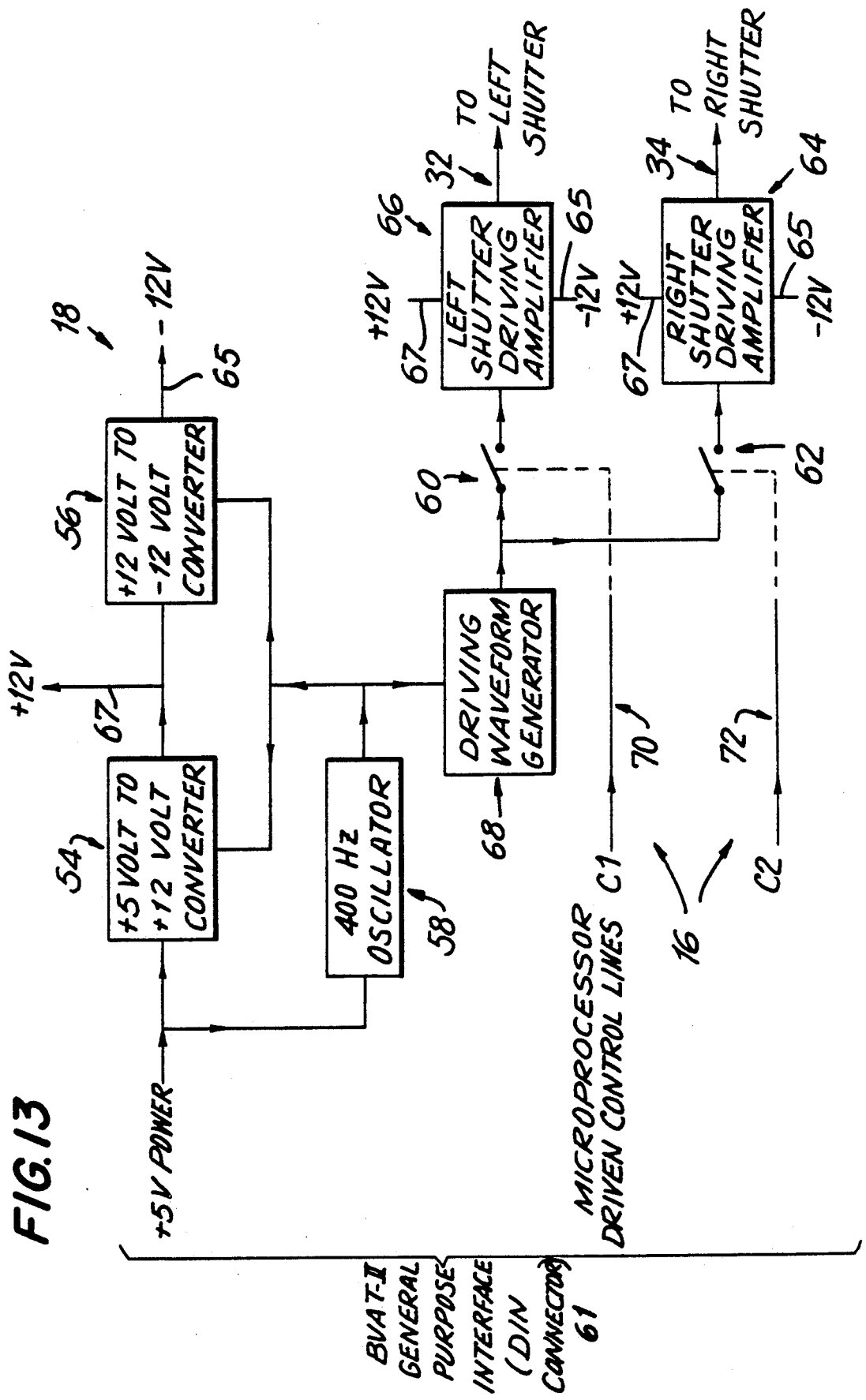

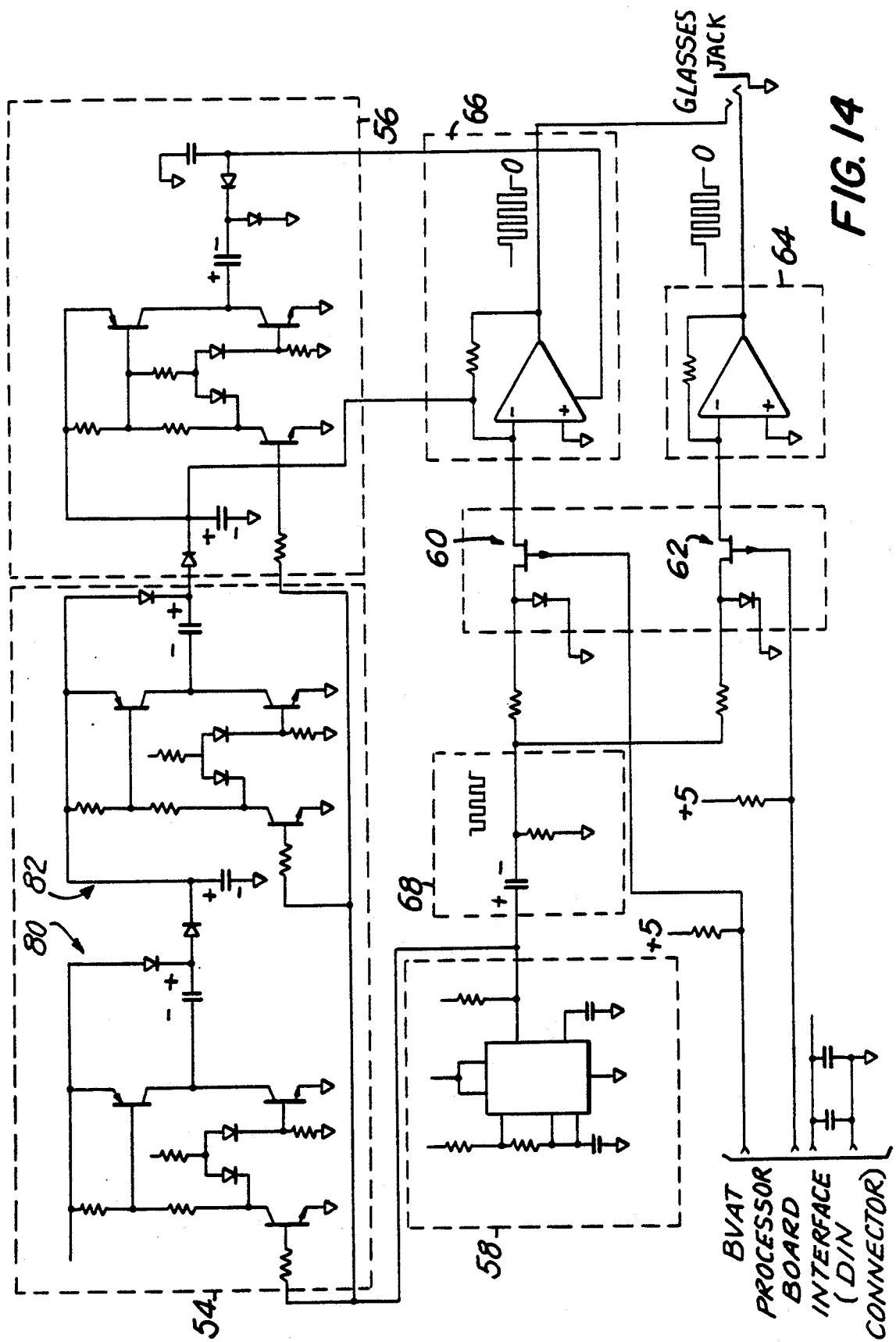

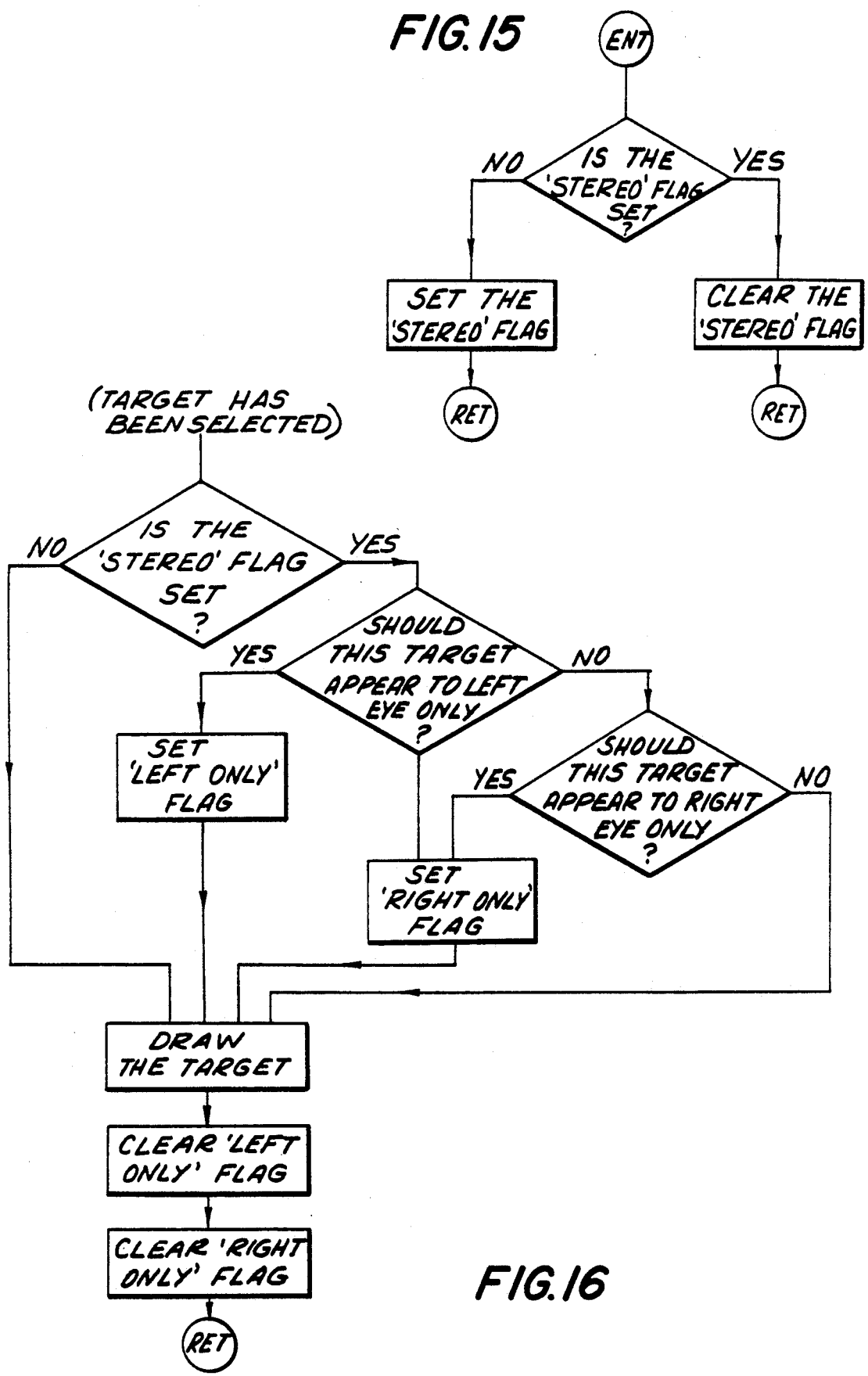

VISUAL FUNCTION TESTER WITH BINOCULAR VISION TESTING

BACKGROUND OF THE INVENTION

The present invention relates to ophthalmic testing instruments, and more particularly, to apparatus and methods for testing the binocular vision of a patient, as well as for testing monocular vision during binocular viewing.

The determination of visual acuity is an essential part of every eye examination. During the course of such an examination, acuity may be measured repeatedly to ascertain the resolution of each eye independently and both eyes together. The determination of binocular function and motor function is an essential part of the process of refracting and determining the optimal corrective lenses as well as providing a means for assessing the progress of ocular pathology.

Originally, clinical methods for measuring visual acuity and binocular function involved the use of wall charts containing a fixed array of Snellen letters, "Tumbling E" targets, and other accepted acuity images and characters or symbols. The patient ordinarily viewed the charts from a fixed distance (usually 20 feet). With the advent of ophthalmic devices, clinical testing methods have become more sophisticated. Electromechanical devices were developed, including the American Optical Project-O-Chart manually operated glass slide projector, and later, a remote controlled glass slide projector. Both types of devices suffered from the inability to present more than a few different visual acuity targets at any given target size. U.S. Pat. No. 4,239,351 solved this problem by disclosing a completely digital electronic apparatus for generating and displaying symbols to be used as targets for testing visual acuity.

The present invention relates to a visual function tester for testing binocular vision, ocular motor imbalance, such as phoria, associated phoria and fixation disparity, and refining binocular refractions. The accurate diagnosis of several ophthalmic disorders requires a binocular testing environment that allows some images to be made visible to one eye and invisible to the other, while some characters may be visible to both eyes. Targets also are generated such that they appear to the patient to be out of the plane of the screen (i.e., they appear to be closer or farther away than the other targets). Such an environment is critical to the diagnosis and treatment of such disorders as, for example, monofixation, fixation disparity, amblyopia, convergence axis, divergence axis, convergence insufficiency, and for detecting malingering.

Previous efforts to provide a test environment closely approximating the normal binocular situation have not proven successful. For example, the four prism-diopter base-out test has been used to determine the existence of bifixation (central fusion) and monofixation (absence of central fusion). While the patient reads letters at a distance of six meters, a four diopter base-out prism is slipped first before one eye and then the other. The prism covered eye is watched closely for movement. Absence of movement by one of the eyes identifies a monocular scotoma in that eye. Bifixation is identified by each eye moving inward to refixate in response to the image displacement produced by the prism. (See *Clinical Ophthalmology*, by Thomas D. Duane, M.D., Ph.D., Vol. 1, Chap. 9, pp. 8 & 10.)

The four diopter base-out prism test has not proven reliable, however, because, occasionally, bifixating patients recognize diplopia when the prism is slipped before either eye, but make no attempt to restore bifixation by convergence. Also, many orthophoric monofixating patients who have good acuity in each eye rapidly alternate their fixation to the uncovered eye as the prism is slipped before the fixating eye; consequently, neither eye shows a movement response.

A second method used to approximate a binocular testing environment employs the A-O Vectographic Project-O-Chart slide (originally manufactured by the American Optical Company). A high resolution, high contrast vectograph printing process is used to produce character slides. Each character on the slide has a self-contained light polarization. When a pair of these polarized characters with axes of polarization 90 degrees to each other are superimposed, each will function independently without optical interference from the other. When the resulting single slide is projected on a non-depolarizing screen and viewed through "analyzers," or polarized glasses, some images are made visible to one eye and invisible to the other. Some portions of the slide also contain characters that are seen by both eyes.

Although the Project-O-Chart slide does provide a more rapid and dependable differentiation than the four diopter base-out prism test, it has not proven successful and has not gained industry acceptance. Production of the character slides and compatible analyzers requires an extremely tight registration of polarization, which is difficult to produce with the high degree of accuracy required for effective operation of the test and which is sensitive to head position. It also suffers from the same deficiencies presented generally by the Project-O-Chart method. There is no flexiblity in the chart printed—the characters on the slide are permanent. As the patient is tested and re-tested, he or she begins to memorize the test characters. Furthermore, dirt on the slide, readjustment of the focus of the projector, and dimming light bulbs are all problems inherent in the Project-O-Chart.

In view of the foregoing, it is an object of this invention to provide improved methods and apparatus for testing binocular vision.

It is a more particular object of this invention to provide methods and apparatus for testing binocular vision that allow an eye examiner quickly and accurately to produce a wide variety of visual targets, including targets which appear to be in front of or behind the surface of the monitor.

SUMMARY OF THE INVENTION

The present invention provides a visual acuity tester with binocular vision testing designed to satisfy the aforementioned needs. The apparatus of the invention includes a high contrast video display monitor with microprocessor control, and storage means for displaying a wide variety of visual acuity characters or images. Thus, unlike previous systems, the invention is not restricted to a fixed number of pre-existing slides (as in the case of the Project-O-Chart). Moreover, the present invention allows the eye examiner to access a wide variety of acuity charts and targets in a fraction of a second, thus providing a more versatile and efficient diagnostic instrument.

Images are made visible to one eye and are concealed from the other through the use of optical shutters controlled in conjunction with the scanning sweeps of the video display monitor. In addition, images are generated which appear to the patient to be either closer or further than the other images appear. Because no polarizer alignment in the display is relied upon, the inefficiencies and expense of those techniques are eliminated. Furthermore, the efficiency and accuracy of the operation of the invention is greatly improved over prior art systems through the use of electronic control means that monitor, control and coordinate the presentation of the images and the opening and closing of the optical shutters.

Accordingly, the present invention relates to apparatus and methods for testing binocular vision having means for generating a plurality of visual acuity targets and a display monitor for displaying the visual targets. The visual function tester also includes electrooptical means for controlling the viewing of the display monitor, and control means to coordinate the optical means and display monitor.

More specifically, the display monitor may be a raster scan cathode ray tube in which even numbered horizontal scan lines and odd numbered horizontal scan lines are displayed during alternate vertical sweeps. The means for generating the plurality of visual acuity targets may be a microprocessor-based unit. The optical means may include liquid crystal shutters to effect a light shutter action in response to related alternate vertical sweeps. Electronic control circuitry may be used to control the liquid crystal shutters in coordination with the vertical sweeps of the display monitor.

BRIEF DESCRIPTION OF THE DRAWINGS

FIG. 5(a) is an illustrative embodiment of a display used for detecting and measuring disassociated phoria.

FIG. 5(b) is an illustrative embodiment of a display used for detecting and measuring associated phoria.

FIG. 6 is the display of FIG. 5(a) as seen by a patient having phoria.

FIG. 11 is a rear partial perspective view of the processor module.

FIG. 12 is an elevational view of a hand-held controller for the video function tester.

FIG. 13 is a block diagram of the glasses driver circuitry.

FIG. 14 is a schematic of the glasses driver circuitry.

FIG. 15 is a flow chart of the software means for invoking binocular vision testing.

FIG. 16 is a flow chart of the software means for selecting concealed targets.

DETAILED DESCRIPTION OF THE PREFERRED EMBODIMENTS

Figure 1:
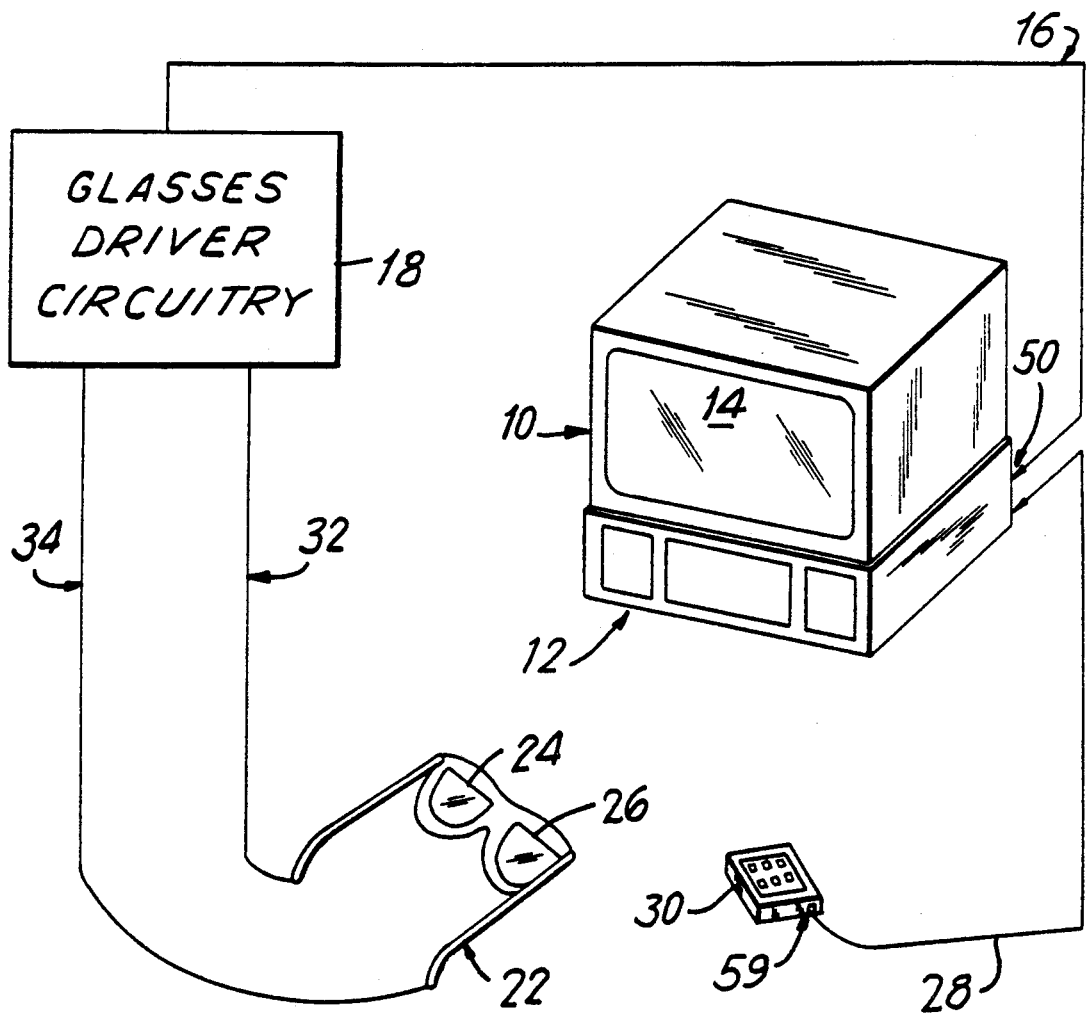
FIG. 1 is a partial perspective view of the major components of the preferred embodiment of this invention.

FIG. 1 shows apparatus for testing visual function by approximating a normal binocular viewing environment, in accordance with the principles of the present invention. The apparatus includes a video display monitor 10 for displaying a plurality of visual targets, processor module 12 for generating and storing a plurality of visual targets, optical means 22 for controlling the viewing of the display monitor, hand-held remote control unit 30 for controlling the display of the visual targets, and control circuitry 18 for coordinating the operation of optical means 22 and the presentation of images on monitor 10.

Video display monitor 10, processor module 12, and hand-held remote control unit 30 may be similar to the apparatus of the visual acuity tester shown in co-pending U.S. patent application Ser. No. 116,709, filed Nov. 3, 1987, which is hereby incorporated by reference herein.

In the preferred embodiment, display monitor 10 is a raster scan cathode ray tube driven by a standard RS170 video signal. The screen of monitor 10 is refreshed at a rate of 30 frames per second. This embodiment of the invention utilizes a scheme known as interlaced scanning, whereby even and odd numbered horizontal scan lines are presented during alternate vertical sweeps. The odd and even numbered scan lines (see lines 36 and 38 shown in FIG. 2), also known as odd and even fields, typically are presented in an alternate or interlaced manner so as to minimize perceived flicker to the viewer.

Figure 2:
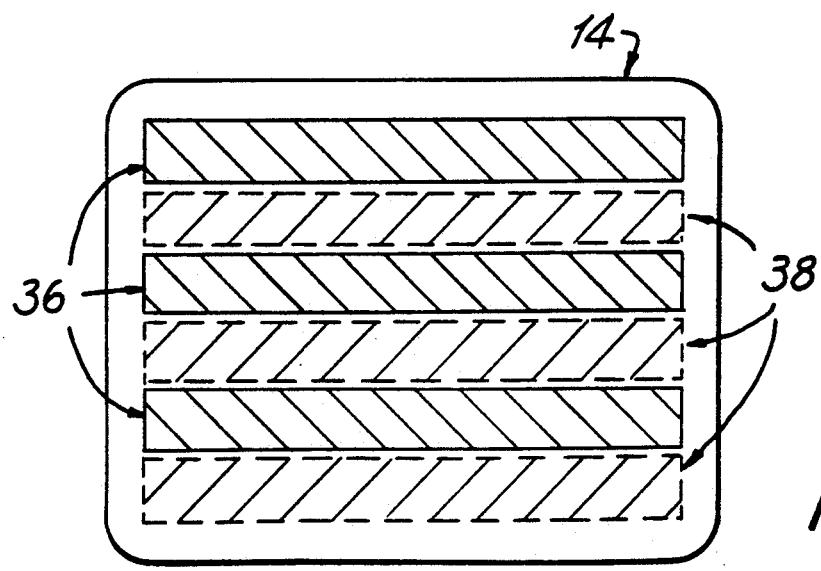
FIG. 2 is a partial, enlarged view of the video sceen of the display monitor.

FIG. 2 shows a partial, enlarged view of the interlaced lines which create a picture on screen 14 of monitor 10. FIG. 2 is only a partial display of screen 14, showing only six interlaced lines. Lines 36 of screen 14 represent scan lines in the odd field. Lines 38 represent scan lines in the even field. A standard video screen has 480 visible interlaced lines. In normal viewing an observer perceives two adjacent fields as being continuous, because the screens are designed such that adjacent lines in alternate fields are related to each other. In the present invention, a given field (e.g., lines 36) may be totally different from its adjacent field (e.g., lines 38).

Interlaced scanning lends itself to the use of glasses for binocular vision testing. Glasses 22 (also referred to as "stereo vision glasses" or "optical means"), as shown in FIG. 1, are constructed with separate apertures for each eye. Each aperture has a shutter 24 or 26 that can transmit or block out light independent of the other shutter. In the preferred embodiment of the invention, shutters 24 and 26 are liquid crystal shutters. The liquid crystal shutters can be opened or closed in approximately one millisecond. The shutters in this embodiment are normally open, and may be closed by applying an AC voltage (preferably a square wave, 20 volts peak-to-peak, at 400 Hertz).

Although the preferred embodiment of the invention uses an interlaced scanning scheme to display information on monitor 10, the invention is not limited to such a scheme. In alternative embodiments, any display system which presents sequential images, including film, may be used. If film is used, alternating frames of the film are made visible to each of a patient's respective eyes. The alternative system must present the images in synchronism with the electro-optical shutters.

Because the odd and even fields are presented on video display 10 during alternate vertical sweeps, the shutter for a particular eye can be opened or closed during a vertical sweep interval either to permit or block that eye's viewing of the next vertical field presented. If the visual information displayed in the odd field is different from the information displayed in the even field, the shutters can be opened or closed such that one eye sees only the odd field, and the other eye sees only the even field. In other words, the shutters can allow a given field to be observed by only one eye, by both eyes, or by neither eye.

For example, to test for bifixation or for suppression, characters can be presented such that one or two characters are missing from the odd field (lines 36 in FIG. 2), but are displayed in the even field (lines 38 in FIG. 2). Different characters are omitted from the even field, and these characters are presented, as well as other characters, in the odd field. Apertures 24 and 26 of optical means 22 are controlled by processor module 12 so that the left eye of the observer sees only the odd field (characters in the even field are concealed) and the right eye sees only the even field (characters in the odd field are concealed).

Figure 3:
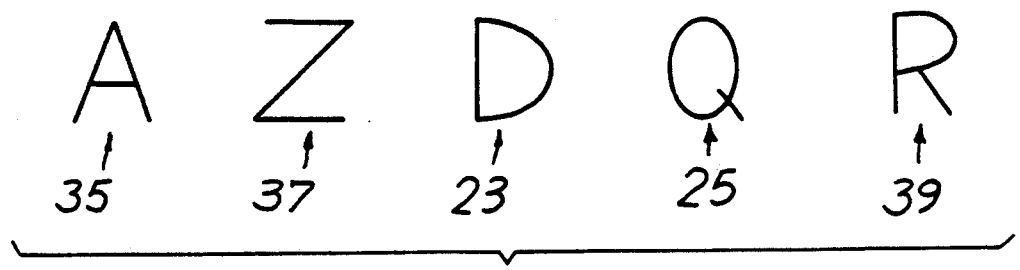
FIG. 3 is an illustrative embodiment of a display used for detecting suppression or bifixation.

FIG. 3 shows an illustrative embodiment of the test for suppression. The characters shown at 37, 23, and 25 are displayed in both the even and odd fields, and are therefore visible to the right and left eyes. The character shown at 35 is displayed only in the even field and is visible to only the right eye. The character shown at 39 is displayed only in the odd field and is visible to only the left eye. Alternatively, the characters displayed at 35, 23, and 39 are displayed in both the odd and even fields, and the characters displayed at 37 and 25 are displayed only in the even and odd fields, respectively.

Patients with normal vision see all of the characters, but patients who suppress one eye will miss a character. The test may be performed with any optotype and size that will allow at least two characters to be displayed. For example, the test may be performed using four 20/40 letters or children's symbols, or using two 20/60 characters.

Figure 4:
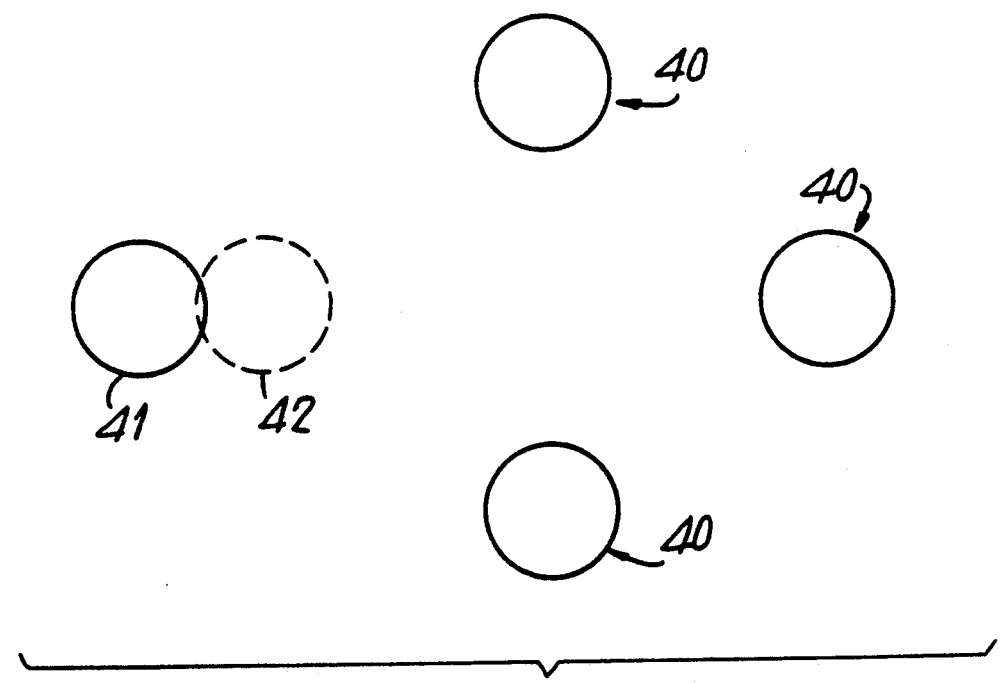
FIG. 4 is an illustrative embodiment of a display used for evaluating stereopsis.

To test for stereopsis, a plurality of acuity targets are presented on the display. At least one target is displayed in the same position to each eye, and at least one target is displayed such that it is displaced laterally. Referring to FIG. 4, the preferred embodiment of the test for stereopsis includes displaying four characters, preferably four 20/80 rings, presented in a diamond-shaped pattern on screen 14 of display monitor 10. Three characters, shown at 40, are displayed in the same position for each eye. The fourth character 41 is displaced laterally, for one or both eyes, to test for stereo acuity. The initial position of character 41 is shown in phantom at 42. Where the character is displaced for both eyes, displacement is in opposite directions for each eye. The patient indicates which character appears out of the plane of screen 14.

Because each eye sees only one field, a person with normal stereopsis will see the shifted character either in front of or behind screen 14. The perceived distance of the character from screen 14 is determined by the magnitude of the horizontal shift. The "Arrow" keys of hand-controller 30 are used to change the amount of lateral displacement. The "Change" key of hand-controller 30 is used to change the position of the displaced character to one of the other three positions on the screen, allowing a patient to be retested at the same degree of stereo acuity. Examples of the software used to generate characters visible only to a preselected eye and to offset a preselected visual target are provided in Appendices C and D.

To screen for phoria, the display of FIG. 5(a) may be shown to a patient. If the patient suffers from phoria, lines 43 and 44 will appear to be displaced from their original positions (shown in FIG. 6 at dotted lines 46 and 47, respectively). Lines 43 and 44 are in one field (either odd or even), and lines 45 are displayed in the other field. Neither eye sees the same image. An image can be displayed to both eyes to serve as a fixation lock (see FIG. 5(b)) to enable the examiner to test for associated phoria. Where black symbols are displayed on a white screen, the screen may serve as the fixation lock.

Figure 7:
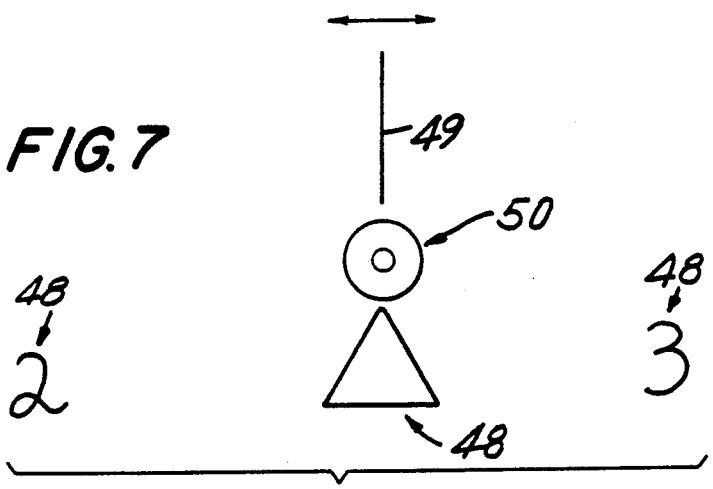
FIG. 7 is an illustrative embodiment of a display used for quantitatively evaluating horizontal fixation disparity.
Figure 8:
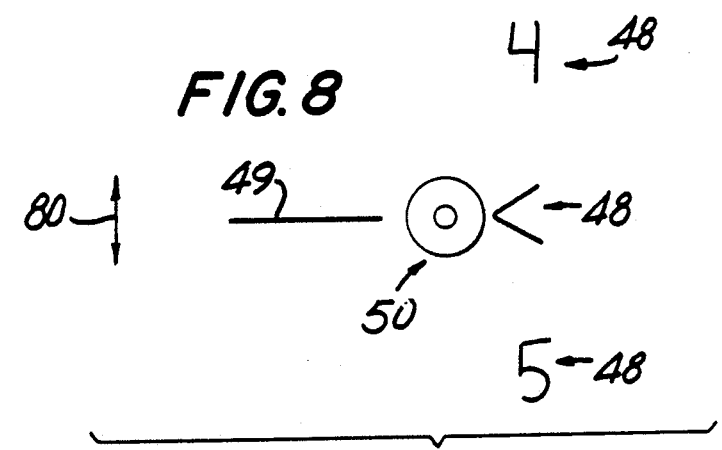
FIG. 8 is an alternative embodiment of a display used for quantitatively evaluating vertical fixation disparity.

In alternative embodiments, shown in FIGS. 7 and 8, a row of characters 48, having a center point, is displayed in either the odd or even field, while a test line 49 is displayed in the other field. The row of characters may be either horizontal (FIG. 7), to test for horizontal imbalance, or it may be vertical (FIG. 8), to test for vertical imbalance, if no fixation lock is displayed. For associated phoria testing, including the screening and quantitative tests, an additional target 50 may be displayed and made visible to both eyes, serving as a fixation lock. The fixation lock may be displayed at any position on the screen. When a fixation lock is displayed, test line 49 may be moved to either side of center (as indicated by bidirectional arrow 80) to evaluate fixation disparity. The displacement of test line 49 from the center (in minutes of angle) provides a quantitative measure of the fixation disparity.

Figure 9:
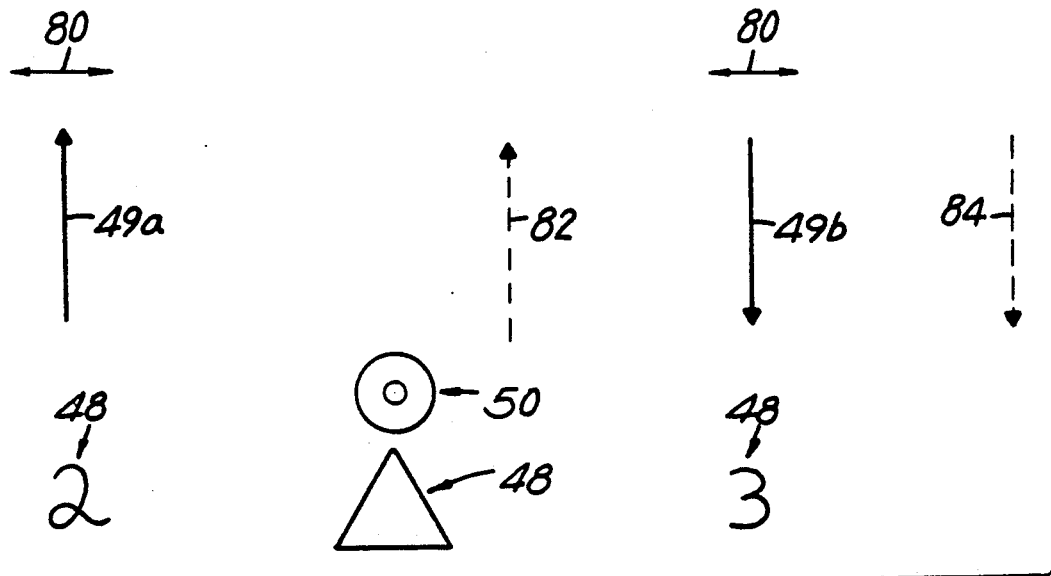
FIG. 9 is an illustrative embodiment of a display used for quantitatively evaluating fixation disparity.

As shown in FIG. 9, two arrows may be used to increase the range of the tests used to evaluate phoria, associated phoria, and fixation disparity. Arrows 49a and 49b are made distinguishable from each other by having one arrow point upward and the other point downward. The arrows are presented at the edges of the screen so that if the patient has a large ocular imbalance, even though one arrow is "moved" off the character line, the second arrow will remain within the range of the character line (shown in FIG. 9 at dotted lines 82 and 84).

Figure 10A:
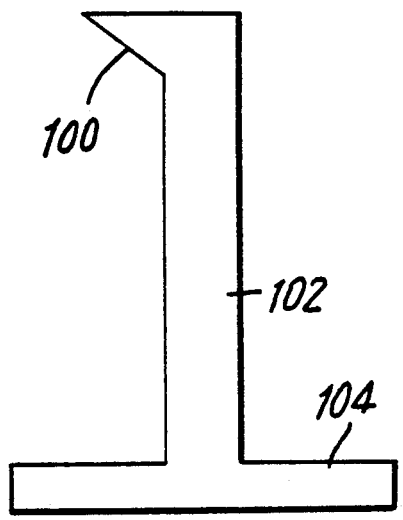
FIGS. 10(a-d) are illustrative embodiments of a display used for evaluating aniseikonia.
Figure 10B:
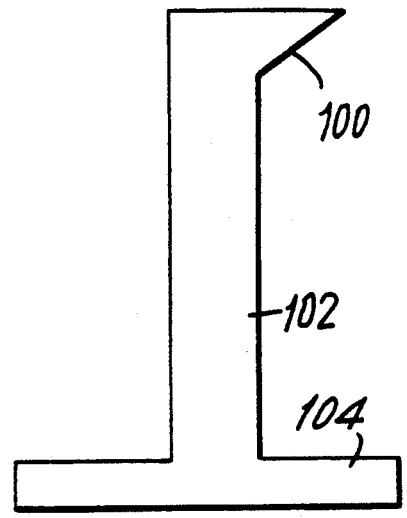

To measure aniseikonia, the display of FIGS. 10(a) and 10(b) may be superimposed and simultaneously shown to a patient. The character of FIG. 10(a) is displayed in the odd field and made visible to the left eye. The character of FIG. 10(b) is displayed in the even field and made visible to the right eye. The height to width ratio of markers 100 may be adjusted to improve the effectiveness of the test. Each target has a marker 100 at the end of the center line 102 that is seen extending from one side by one eye and extending from the other side by the other eye. Each target has fusion lock 104 at the other end of center line 102. A patient with normal vision sees equal image sizes with each eye, and will set the markers at the same distance from fusion lock 104 (FIG. 10(c)). A patient with aniseikonia will see one marker further from the fusion lock than the other (FIG. 10(d)). The distance of one of the markers to the fusion lock can be altered until the patient perceives both of markers 100 as being equidistant to the fusion lock. The ratio of the two distances is a measure of aniseikonia.

Figure 10C:
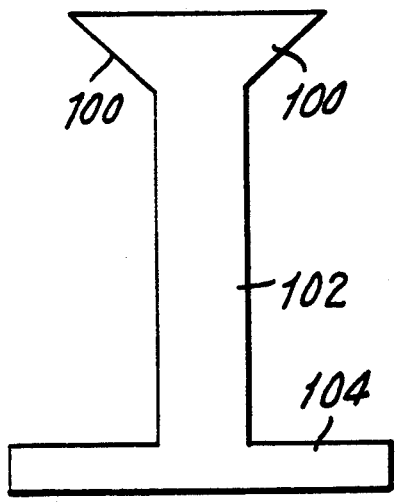
Figure 10D:
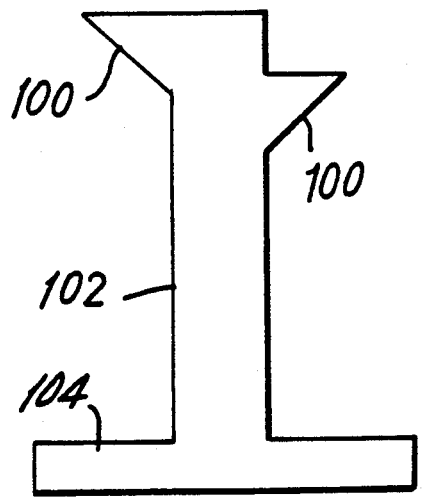

This test can be performed at various angles. For example, this test can be performed with the measured distance 90 degrees to the horizontal (as shown in FIG. 10(c)), at 45 degrees, or with the measured angle horizontal (0 degrees) and the fusion lock vertical.

Processor module 12, shown in FIG. 1, includes means for generating the plurality of visual acuity targets. Module 12 is a microprocessor based system, which includes a dynamic bit-mapped graphics memory. Module 12 has two complete screens of memory, either of which can be displayed on monitor 10. The microprocessor of module 12 reads from and writes to the bit-mapped graphics memory, from which the information is transmitted to screen 14 of monitor 10. The bit-mapped memory feature is described in further detail in co-pending U.S. patent application Ser. No. 116,709, previously incorporated herein by reference.

Shutters 24 and 26 of stereo vision glasses 22 operate in conjunction with the visual information displayed on screen 14 at any particular time. The synchronization of the shutters and the vertical sweeps of the monitor are controlled by the microprocessor of module 12. The microprocessor of module 12 transmits control signals through line 16 to the glasses driver circuitry 18 via a general purpose interface connector 61. In the illustrative embodiment, a DIN connector is used as connector 61.

In the preferred embodiment, control signals for optical shutters 24 and 26 are generated in the microprocessor by operating software specifically designed to perform a series of ophthalmic tests. Flow charts of the computer programs for implementing this invention are provided in FIGS. 15–20, and are described below. Software programs which execute these flow charts appear in the appendices. In an alternative embodiment, the microprocessor of module 12 generates control signals in response to instructions received from the eye examiner. The eye examiner may directly control the operation of optical shutters 24 and 26 or, alternatively, the shutters may operate according to a pre-programmed series of video displays. In still another alternative embodiment, shutters 24 and 26 are hard-wired to module 12 and are operated without the use of software. The shutters are driven by an address line from the CRT controller which indicates whether an odd or even field is being presented.

FIG. 11 shows a rear view of processor module 12. Module 12 includes various interfaces for connecting system components and accessories. Video display monitor 10 connects to module 12 via interface means 53 and 55, supplying power and video signals, respectively, to monitor 10. Interface connector 61 accepts the connection of communication line 16. In the preferred embodiment, both control signals and electrical power are sent from module 12 to the glasses driver control circuitry 18 via line 16.

Hand-held controller 30 is shown in detail in FIG. 12. Cable connection 59 accepts cable 28 in order to connect controller 30 to module 12. The distal end of cable 28 connects with keypad interface 52 of module 12. Controller 30 is used by the eye examiner to present a variety of visual acuity images on monitor 10. The detailed functions and operations of controller 30 are described in greater detail in co-pending U.S. patent application Ser. No. 116,709.

Glasses driver circuitry 18 powers shutters 24 and 26 of optical means 22 in response to control signals received from processor module 12 via communication line 16. Driver circuitry 18 is connected to optical means 22 such that shutters 24 and 26 may be independently controlled. Circuit 18 and optical means 22 (shown in FIG. 1) may be connected by two communication lines 32 and 34 such that the lines control shutters 24 and 26, respectively.

The components of circuit 18 are shown in block diagram form in FIG. 13. Circuit 18 includes voltage converter 54, voltage inverter 56, oscillator 58, waveform generator 68, and shutter driving amplifiers 64 and 66. In an illustrative embodiment, power is supplied at a low voltage, preferably at five volts, via line 16. The voltage is applied to voltage converter 54 and oscillator 58. Voltage converter 54 includes a voltage multiplier circuit to convert the five-volt supply to a twelve-volt supply. The twelve-volt supply is output to amplifiers 64 and 66 via line 67. Voltage inverter 56 includes a circuit which inverts the voltage applied to its terminals. The inverted voltage is output to amplifiers 64 and 66 via line 65. Oscillator 58 creates an AC voltage waveform, preferably with a frequency of 400 Hertz. The output signals from oscillator 58 are connected to waveform generator 68. In the preferred embodiment, waveform generator 68 includes a series capacitor and a shunt resistor (connected to ground), which eliminate the DC portion of the oscillator output signal. Two control signals 70 and 72 (both transmitted on communication line 16) operate switches 60 and 62, preferably electronically controlled, to activate left and right shutter amplifiers 66 and 64, respectively. When switches 60 and 62 are closed, the signals from waveform generator 68 are sent to amplifiers 64 and 66. The outputs of amplifiers 64 and 66 are sent to shutters 24 and 26 via lines 32 and 34.

FIG. 14 shows a detailed circuit diagram of the preferred embodiment of glasses driver circuitry 18. In this embodiment, voltage converter 54 includes a two stage voltage multiplier which supplies twelve volts to voltage inverter 56 and to an operational amplifier integrated circuit chip (used for amplifiers 66 and 68). The NPN and PNP transistors used in these circuits may be 2N3904 and 2N3906 transistors, respectively.

Oscillator circuit 58 includes a "555" integrated circuit timer, resistors, and capacitors. Oscillator 58 provides the AC signal input to voltage converter 54 and and inverter 56. The output signal of oscillator 58 is also fed to driving waveform generator 68, which eliminates any DC component of the signal. The remaining AC component feeds the negative input of amplifiers 66 and 64 when switches 60 and 62 are "closed." Switches 60 and 62 preferably are junction field effect transistors (JFETs) which are electronically switched "open" or "closed" via control lines 70 and 72. Each of amplifiers 66 and 64 include an operational amplifier with a 422K ohm resistor connected to form a negative feedback loop. The outputs of the amplifiers drive optical means 22.

In an alternative embodiment, glasses driver circuitry 18 and optical means 22 are replaced with stereo vision glasses and driving circuitry of a type such as have been commercially available from Haitex Resources, Inc., 208 Carrollton Park #1207, Carrollton, Tex. 75006. The Haitex glasses driver circuit has only one control line which provides only for one shutter being open, while the other is closed. Unlike circuit 18 and optical means 22, which independently control apertures 24 and 26, the Haitex glasses do not provide the option of simultaneously opening both apertures or closing both apertures.

FIG. 15 shows a flow chart of software means for invoking or deactivating binocular vision testing when a predetermined key sequence is entered, preferably from hand controller 30. The software causes module 12 to check the status of binocular vision testing. If binocular vision testing is disabled, the software causes the visual acuity tester to begin binocular vision testing. If binocular vision testing is enabled, the software terminates binocular testing and returns to ordinary visual acuity testing.

FIG. 16 shows a flow chart of software means for selecting "concealed" target testing. The software selects the field (odd, even or both) which will be used to display a preselected character (and therefore, selects whether the character will be visible to only one or to both eyes). The software first checks whether binocular vision testing is enabled. If it is not, an ordinary visual acuity target is drawn. If binocular testing is enabled, the software determines whether the target should appear to only one or to both eyes, and sets the appropriate software flag. After the target is eventually drawn, the software clears these flags. Sample software code implementing these functions is provided in Appendix A.

Figure 17:
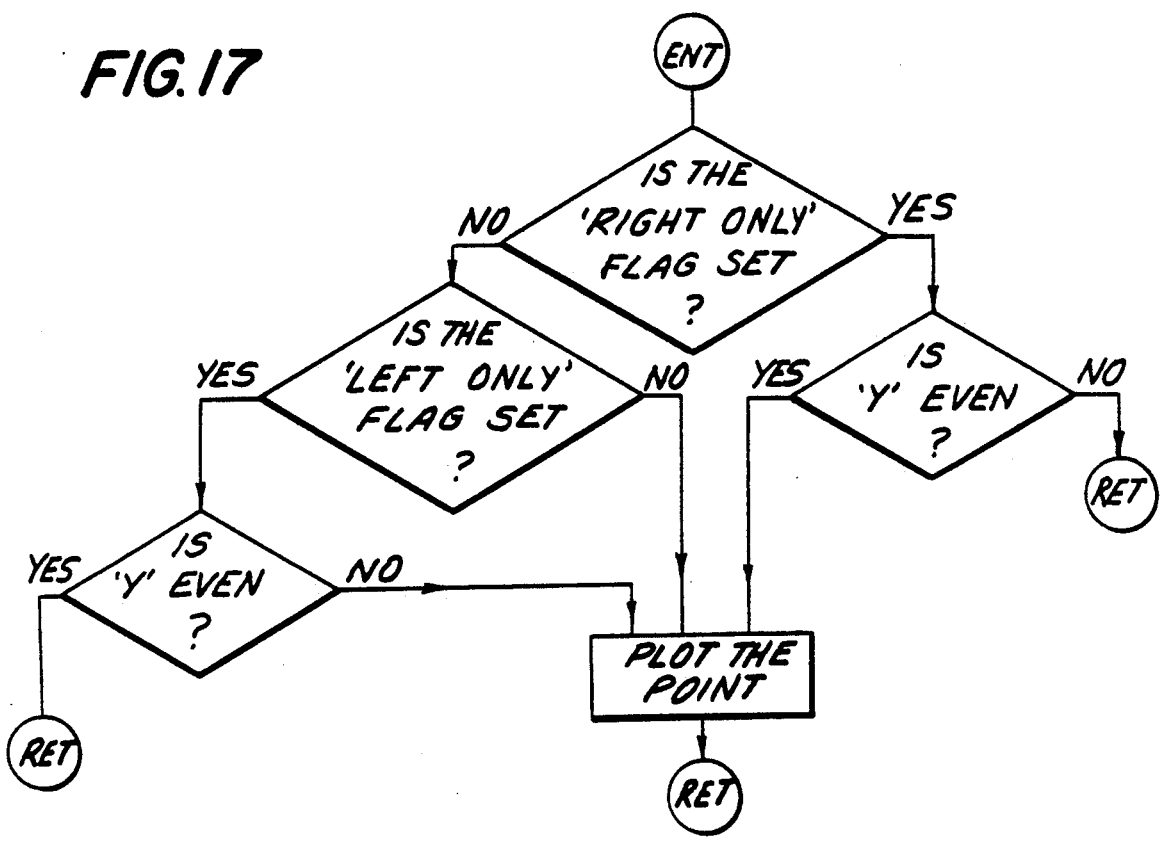
FIG. 17 is a flow chart of the software means for creating concealed targets.

FIG. 17 shows a flow chart of software means for creating concealed targets. The software creates characters in graphics memory for display in the odd or even field or in both fields. In the preferred embodiment, targets appearing only to the right or left eye are drawn only on even-numbered (even field) or odd-numbered (odd field) horizontal raster lines, respectively. Targets appearing to both eyes are drawn in both fields. Using the flags set by the software shown in FIG. 16, the software of FIG. 17 determines whether a given target is to be plotted on even or odd raster lines, or on both. Sample software code implementing these functions is provided in Appendix B.

Figure 18:
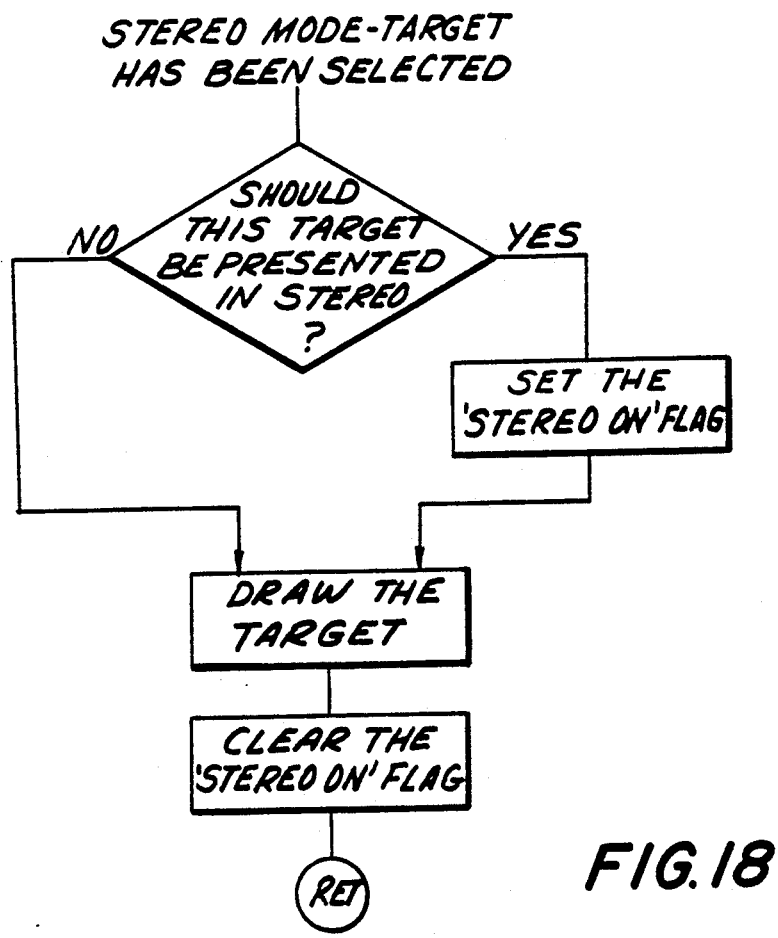
FIG. 18 is a flow chart of the software means for selecting depth targets.
Figure 19:
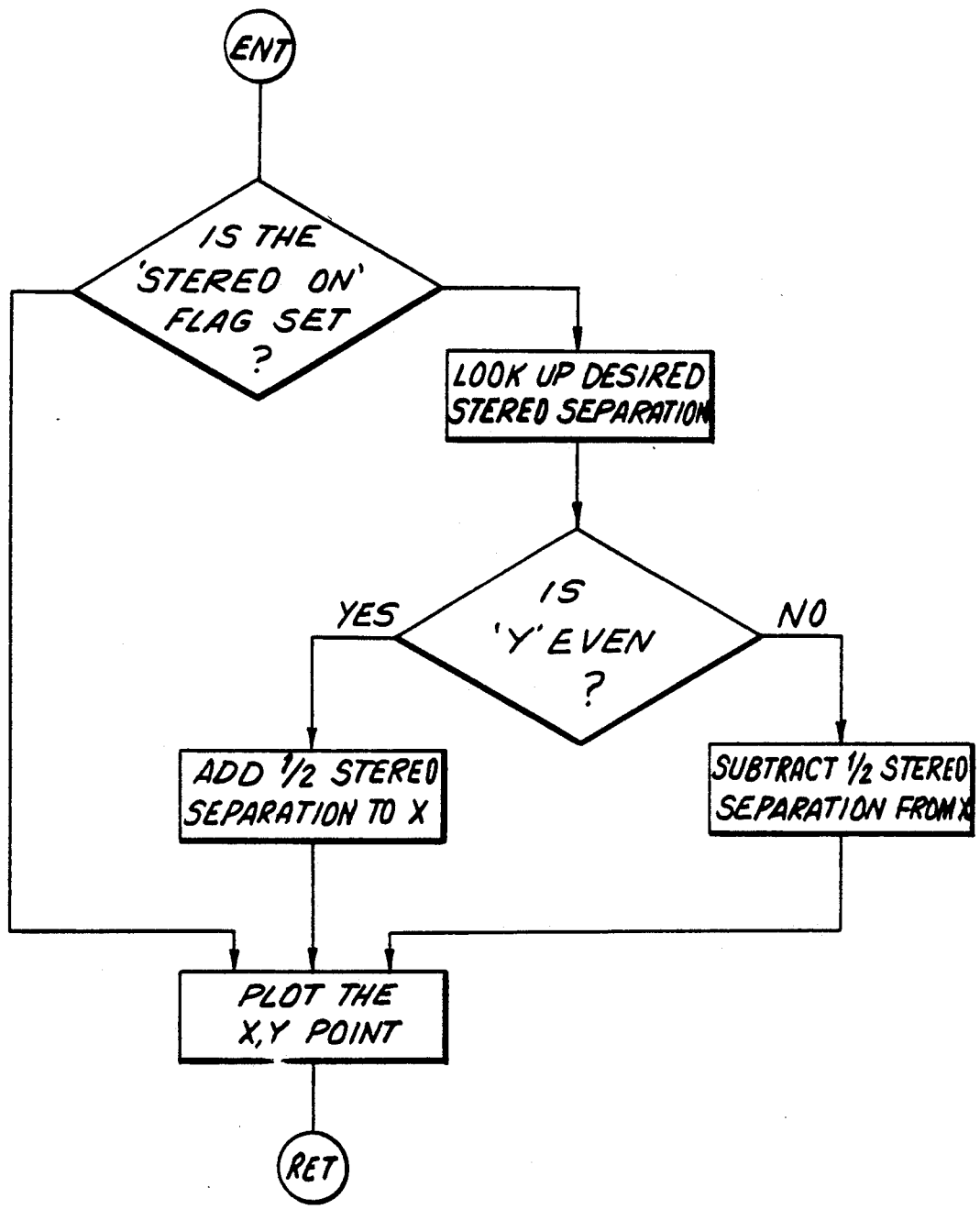
FIG. 19 is a flow chart of the software means for creating depth targets.

FIG. 18 shows a flow chart of software means for selecting "depth" target testing. If binocular vision testing is desired, the software sets a flag, such as the "stereo-on" flag, for use by the depth target creation software (FIG. 19). If binocular vision testing is not desired, the flag is not set, and an ordinary target is drawn. Sample software code implementing these functions is provided in Appendix C.

FIG. 19 shows a flow chart of software means for creating depth targets. A target created by this software is made visible to both eyes, but each eye sees a different image. The image presented to the right eye is identical to that presented to the left eye, but it is laterally displaced. The images are alternately displayed to the right and left eyes. The lateral displacement of the images creates the appearance of depth. The examiner selects a desired stereo separation, and the software modifies the plot coordinates in graphics memory to display the images to the right and left eyes with the desired separation. Software code implementing these functions is provided in Appendix D.

Figure 20:
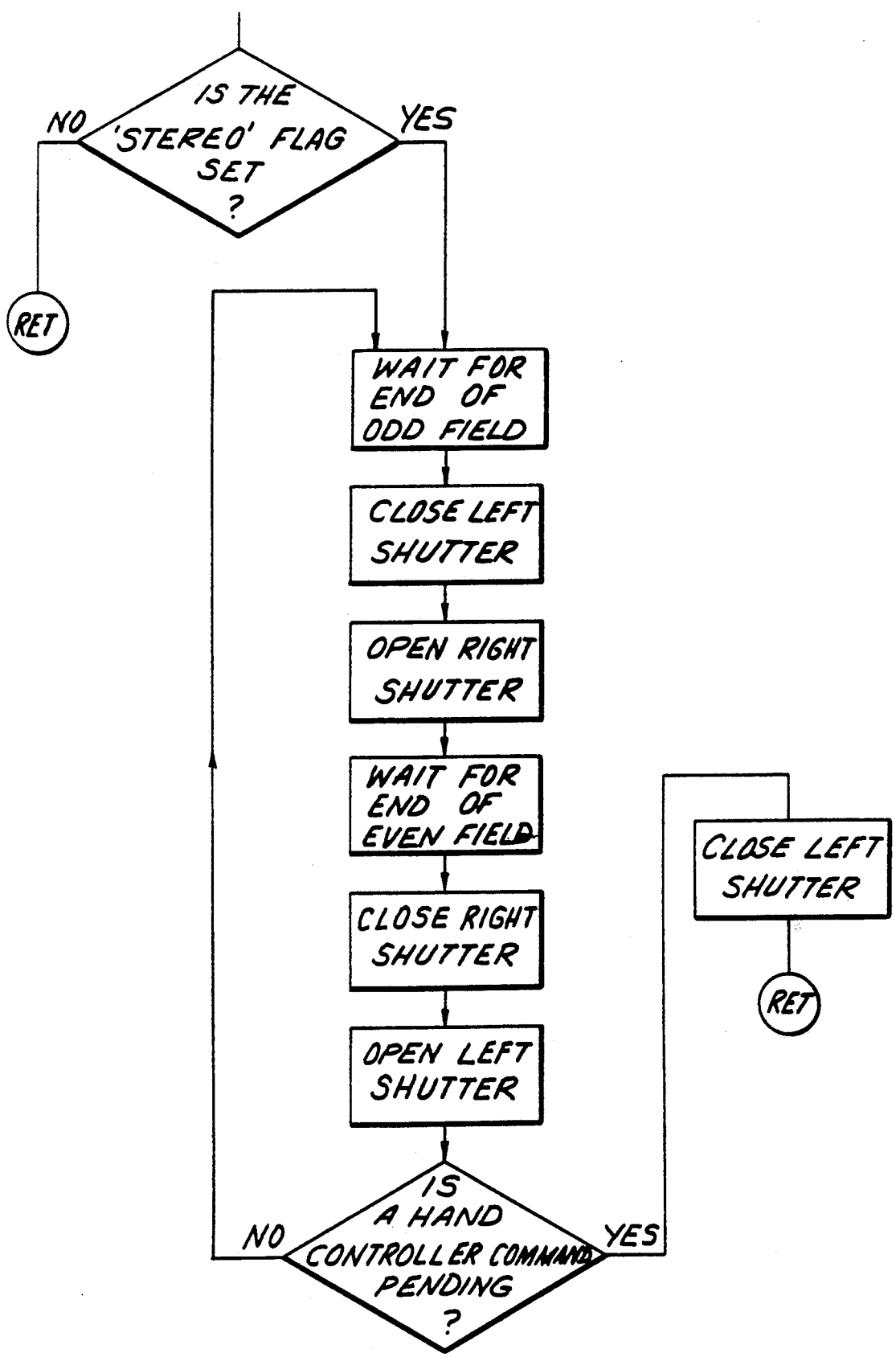
FIG. 20 is a flow chart of the software means for driving the glasses used in binocular vision testing.

FIG. 20 shows a flow chart of the software means for synchronizing the optical means and driver circuitry with the display of the alternating fields on the monitor. This software first determines whether binocular vision testing is enabled. If it is, the software causes module 12 to wait for the end of the odd field, and then closes aperture 24 (the left aperture) and opens aperture 26 (the right aperture). Module 12 then waits for the end of the even field, closes aperture 26, and opens aperture 24. At the end of this sequence, the software determines whether a command entered via hand-controller 30 is pending. If there is no command pending, the software repeats the above sequence, and continues to do so until it detects a pending command. Once a pending command is detected, the program closes both apertures, thereby preventing the viewer from seeing the next target. This last step is not possible with the Haitex glasses. Because only one control line is provided with the Haitex glasses, when a given aperture is open, the other aperture is closed. When using the Haitex glasses, screen 14 must be kept blank whenever it is desirable to prevent the viewer from seeing the next character. Software code for synchronizing the optical means with the display of the alternating fields is provided in Appendix E.

It is thought that the video acuity tester with binocular vision testing apparatus and the methods of the present invention and its attendant advantages will be understood from the foregoing description and it will be apparent that various changes may be made in the form, construction and arrangement of the parts thereof without departing from the spirit and scope of the invention.

APPENDIX A

```
L4I:      CMP STEREO_TEST,2        ;MALINGERING MODE ?
          JNE C_MAL1               ;
;
;WE ARE IN MALINGERING MODE - THE SECOND CHARACTER SHOULD
; APPEAR TO THE RIGHT EYE ONLY, AND THE SECOND FROM THE
; LAST CHARACTER SHOULD APPEAR TO THE LEFT EYE ONLY
;
; DI HAS THE CHARACTER NUMBER IN THE LINE BEING CONSIDERED
;
          CMP DI,4                 ;DO WE HAVE AT LEAST 4
                                   ;CHARACTERS IN THE
                                   ;LINE?
                                   ;JUMP IF NOT - NOT
          JB C_MAL1                ;ENOUGH CHARACTERS
```

```
;
; WE HAVE 4 OR MORE CHARACTERS
;
        CMP HORIZ_LINE,0        ;FIRST LINE?
        JNE C_MAL1              ;JUMP IF NOT - ONLY
                                ;DONE IN THE FIRST
                                ;LINE

;
; THIS IS THE FIRST LINE
;
        CMP HORIZ_NUM,1         ;IS THIS THE SECOND
                                ;CHARACTER?
        JNE C_MAL2              ;JUMP IF NOT
;
;IT'S THE SECOND CHARACTER
;
        MOV RIGHT_ONLY,1        ;MAKE IT RIGHT ONLY
        JMP C_MAL1              ;
;
;
;NOT THE SECOND CHARACTER
;
C_MAL2: PUSH DX                 ;SEE SECOND FROM LAST
        MOV DX,DI               ;CHARACTER - USE DX
        SUB DX,2                ;FOR CALCULATION
        CMP HORIZ_NUM,DL        ;
        JNE C_MAL3              ;JUMP IF NOT
;
;IT'S THE SECOND FROM THE LAST CHARACTER
;
        MOV LEFT_ONLY,1         ;MAKE IT LEFT ONLY
;
C_MAL3: POP DX                  ;RESTORE DX
;
C_MAL1: CALL DRAW               ;DRAW A CHARACTER
```

APPENDIX B

IN A SEPARATE EYES MODE (STEREO_TEST =2,3, OR 4)

```
        CMP RIGHT_ONLY,1        ;ARE WE A SEPARATE
                                ;EYES MODE SPECIAL?
        JNE CONT_T              ;JUMP IF NOT -
                                ;CONTINUE AS USUAL TO
                                ;PLOT THE POINT
;
;WE ARE IN RIGHT ONLY MODE
;
        TEST BX,1               ;CHECK LSB OF LINE
                                ; NUMBER
        JZ CONT_S               ;CONTINUE TO PLOT THE
                                ; POINT IF EVEN
        JMP EXITP               ;EXIT (SKIP) IF ODD
;
```

```
CONT_T:     CMP LEFT_ONLY,1         ;SEPARATE EYES MODE
                                    ; SPECIAL?
            JNE CONT_V              ;JUMP IF NOT
;
;WE ARE IN LEFT ONLY MODE
;
            TEST BX,1               ;CHECK LSB OF LINE
                                    ; NUMBER
            JZ EXITP                ;JUMP (SKIP) IF EVEN
            JMP CONT_S              ;OTHERWISE CONTINUE AS
                                    ; NORMAL - PLOT THE
                                    ; POINT
```

APPENDIX C

```
;STEREO_TEST = 1 - THIS IS STEREOPSIS MODE - DRAW THE FOUR
;O'S
;
;
C_0:        MOV M_L_SIZE,8          ;ESTABLISH THE
                                    ; CHARACTER SIZE
            MOV L_SIZE,8            ;
            CALL SET_SCALE          ;
            CALL TAKE               ;TAKE CONTROL OF THE
                                    ;SCREEN MEMORY D-RAM
;
;THE FOLLOWING CODE DETERMINES WHICH OF THE FOUR O'S IS IN
;STEREO
;
            MOV AH,FIRST_CALL_S     ;SEE IF FIRST CALL
            AND AH,FIRST_CALL       ;
            JZ CT5                  ;JUMP IF RANDOM

;
;NOT RANDOM - TOP O SHOULD BE STEREO
;
            MOV AX,1                ;CHOOSE POSITION #1
            JMP CT6                 ;
;
; CHOICE IS RANDOM - PICK A NUMBER
;
CT5:        CALL RAND               ;GET A RANDOM NUMBER
            XOR DX,DX               ;AND SCALE IT TO A
                                    ;VALUE BETWEEN O AND
                                    ;3
            MOV BX,16384            ;
            DIV BX                  ;AX GETS O TO 3

CMP AL, LAST_CHOICE     ;SAME AS LAST TIME? -
                                    ; DON'T WANT SAME
                                    ; POSITION
            JE CT5                  ;TRY AGAIN IF SO
;
CT6:        MOV LAST_CHOICE,AL      ;CHOICE IS IN AL
            MOVE STEREO_CHAR,AL     ;STORE FOR DISPLAY
                                    ; ROUTINE
```

```
;
;
;
; NOW DRAW O'S
;
            CMP AL,0                    ;IS THIS THE ONE TO DO
                                        ; STEREO IN ?
            JNE CT1                     ;JUMP IF NOT
;
            MOV STEREO_ON,1             ;OTHERWISE MAKE IT
                                        ; STEREO
;
CT1:        DEC AL                      ;DECREMENT FOR NEXT
                                        ; POSITION
;
            MOV X_ORG,215               ;X,Y ORIGINS FOR TOP
                                        ;POSITION
            MOV Y_ORG,83                ;

PUSH AX                     ;SAVE AX - CALLED
                                        ;ROUTINE MODIFIES IT
            CALL O                      ;DRAW THE 'O'
            POP AX                      ;RESTORE AX
;
            MOV STEREO_ON,0             ;CANCEL STEREO IF IT
                                        ; WAS ON
;
;
;
            CMP AL,0                    ;IS THIS THE ONE TO DO
                                        ; STEREO IN?
            JNE CT2                     ;JUMP IF NOT
;
            MOV STEREO_ON,1             ;OTHERWISE MAKE IT
                                        ; STEREO
;
CT2:        DEC AL                      ;DECREMENT FOR NEXT
                                        ; POSITION
;
            MOV X_ORG,142               ;X,Y ORIGINS FOR LEFT
                                        ; POSITION
            MOV Y_ORG,156               ;

PUSH AX                     ;SAVE AX
            CALL O                      ;DRAW THE 'O'
            POP AX                      ;RESTORE AX
;
            MOV STEREO_ON,1             ;CANCEL STEREO IT IF
                                        ; WAS ON
;
;
;
            CMP AL,0                    ;IS THIS THE ONE TO DO
                                        ;STEREO IN?
            JNE CT3                     ;JUMP IF NOT
;
            MOV STEREO_ON,1             ;OTHERWISE MAKE IT
```

```
CT3:        DEC AL                  ;STEREO
                                    ;DECREMENT FOR NEXT
                                    ; POSITION
            MOV X_ORG,289           ; X,Y ORIGINS FOR
                                    ; RIGHT POSITION
            MOV Y_ORG,156           ;
;
            PUSH AX                 ;
            CALL O                  ;DRAW THE 'O'
            POP AX                  ;
;
            MOV STEREO_ON,0         ;CANCEL STEREO IF IT
                                    ; WAS ON
;
;
;
            CMP AL,0                ;IS THIS THE ONE TO DO
                                    ;STEREO IN?
            JNE CT4                 ;JUMP IF NOT
;
            MOV STEREO_ON,1         ;OTERWISE MAKE IT STEREO
;
CT4:        MOV X_ORG,215           ;X,Y ORIGINS FOR BOTTOM
                                    ;POSITION
            MOV Y_ORG,230           ;

PUSH AX                 ;
            CALL O                  ;DRAW THE 'O'
            POP AX                  ;
;
            MOV STEREO_ON,0         ;CANCEL STEREO IF IT WAS
                                    ;ON
;
            JMP EXIT2               ;ALL DONE
;
```

APPENDIX D

```
CONT_U:     CMP STEREO_ON,1         ;ARE WE DOING STEREO ?
            JNE CONT_S              ;JUMP IF NOT
;
;WE ARE DOING STEREO - OFFSET EVEN NUMBERED LINES TO THE
;RIGHT, AND ODD NUMBERED LINES TO THE LEFT
;
            PUSH DX                 ;SAVE REGISTER USED
;
;LOOK UP SPACING IN THE TABLE
;
            PUSH BX                 ;
            PUSH ES                 ;
;
            MOV BX,CS               ;POINT ES TO TABLE FOR
                                    ; LOOKUP
            MOVE ES,BX              ;
;
```

```
        XOR BH,BH
        MOV BL,STEREO_SPACING       ;BX HAS SPACING NUMBER
;
        MOV DL,ES:SPACING[BX]       ;FETCH VALUE INTO DL
;
        POP ES                      ;RESTORE REGISTERS
        POP BX                      ;
;
;
        MOV DH,DL                   ;SAVE SPACING IN DH
        SHR DL,1                    ;DIVIDE BY TWO =>
                                    ;OFFSET TO EITHER SIDE
;
        TEST BL,1                   ;IS THIS AN ODD
                                    ; NUMBERED LINE?
        JZ EVENX                    ;JUMP IF EVEN
;
;THIS IS AN ODD NUMBERED LINE
;
;IF STEREO_SPACING IS ODD, WE WILL TAKE THE EXTRA COUNT HERE
;ON THE ODD NUMBERED LINE
;
        AND DH,1                    ;MASK THE LSB
        ADD DL,DH                   ;ADD ON IF SET
;
        XOR DH,DH                   ;DX HAS THE OFFSET
                                    ; RESULT
        SUB AX,DX                   ;ADJUST X POSITION TO
                                    ; LEFT
;
        POP DX                      ;RESTORE DX
        JMP CONT_S                  ;AND CONTINUE - PLOT
                                    ; THE POINT ON THE
                                    ; SCREEN
;
;
; THIS IS AN EVEN NUMBERED LINE
;
EVENX:  XOR DH,DH                   ;DX HAS THE OFFSET
                                    ; RESULT
        ADD AX,DX                   ;ADJUST X POSITION
                                    ; TO RIGHT
;
        POP DX                      ;RESTORE DX - PROCEED
                                    ; WITH PLOTTING THE
                                    ; POINT
;
;
```

APPENDIX E

```
;
;
TOGGLE     PROC NEAR                ;*********************
;
;PROCEDURE TO TOGGLE THE STEREO INTERFACE LINES FOR STEREO
;MODE
```

```
;           PUSH AX                      ;SAVE REGSTERS USED
            PUSH CX                      ;
;
            CMP STEREO_TEST,0            ;ARE WE DOING A STEREO
                                         ; TEST?
            JNE LP_INT1                  ;PROCEED IS SO
            JMP CXXX                     ;JUMP IF NOT - EXIT
;
;
; WE ARE DOING STEREO - TOGGLE THE INTERFACE LINES
;
;
;WAIT FOR 11 VERTICAL INTERVALS TO MAKE SURE WE WON'T BE
;INTERRUPTED BY COMPLETION OF THE CURRENT INCOMING KEYBOARD
;COMMAND
;
LP_INT1:    MOV KEY_INT,0                ;CLEAR THE FLAG - WILL
                                         ; BE SET BY KEYBOARD
                                         ; INTERRUPT
            MOV CX, 11                   ;11 VERTICALS TO WAIT

LP_INT2:    CALL V_WAIT                  ;WAIT FOR A VERTICAL
                                         ; INTERVAL
            MOV AL,KEY_BUF               ;EXIT IF KEYBOARD
                                         ; COMMANDS ARE PENDING
            OR AL,KEY_BUF_C              ;
            JZ C_CX                      ;PROCEED IF NONE
                                         ; PENDING
            JMP C_C                      ;OTHERWISE ABORT
;
C_CX:       CMP KEY_INT,0                ;IS FLAG AS WE LEFT
                                         ; IT?
            JNE LP_INT1                  ;IF NOT, START OVER
;
            LOOP LP_INT2                 ;OTHERWISE CONTINUE
                                         ; TILL 11 VERTICAL
                                         ; INTERVALS COMPLETED
;
;DROPPING THRU MEANS WE WENT 11 VERTICAL INTERVALS WITHOUT A
;KEYBOARD INTERRUPT
;
;
;BE SURE D-RAM IS UNDER CONTROL OF CRTC CHIP - WE ARE ABOUT
;TO GO A LONG TIME WITHOUT INTERRUPTS.  SHOULD ALREADY BE
;CLEARED - THIS IS TO MAKE SURE
;
            PUSH AX                      ;SAVE AX
            MOV AL,XR5                   ;FETCH RAM IMAGE OF
                                         ;EXTERNAL REGISTER
            AND AL,7FH                   ;CLEAR THE BIT
            CLI                          ;INTERRUPTS OFF WHILE WE
            OUT 5,AL                     ;UPDATE THE REGISTER
            MOV XR5,AL                   ;AND ITS IMAGE
            STI                          ;INTERRUPTS BACK ON
                                         ; AGAIN
            POP AX                       ;RESTORE AX
```

```
;PROCEED WITH ODD/EVEN FIELD DETERMINATION - THIS IS DONE
;BY SAMPLING "DE" (DISPLAY ENABLE) FROM THE CRTC CHIP AT A
;SPECIFIC TIME FOLLOWING THE VETICAL SYNC "VS" PULSE.  "DE"
;WILL BE EITHER HIGH OR LOW AT THAT TIME DEPENDING UPON THE
;FIELD BEING SAMPLED
;
;
          CLI                       ;NO INTERRUPTS TILL WE
                                    ;FIGURE OUT ODD/EVEN
                                    ;FIELD

CALL V_WAIT               ;WAIT A VERTICAL INTERVAL
;
L_I:      CALL V_WAIT               ;AND AGAIN
;
          MOV CX,560                ;WAIT A WHILE - MAGIC
                                    ;TIME TO 'DE' SAMPLING
LPW:      NOP                       ;TIMING LOOP
          LOOP LPW                  ;
;
          IN AL,4                   ;BRING IN DE
          TEST AL,4                 ;LOOK AT DE
          JZ L_I                    ;JUMP IF LOW - TRY
                                    ;NEXT FIELD
;
;DROPPING THRU INDICATES WE HAVE THE STARTING FIELD THAT WE
;WANT - DE IS HIGH
;
          STI                       ;INTERRUPTS BACK ON
;
;
;
          MOV AL,XR2                ;GET IMAGE OF REGISTER
                                    ;WHICH CONROLS STEREO
                                    ;GLASSES
          AND AL,3FH                ;CLEAR EXISTING BITS
                                    ;FOR RIGHT AND LEFT
                                    ;EYES
          OR AL,80H                 ;SET ONE BIT DIFFERENT
                                    ;(ONE EYE OPEN)
;
          CLI                       ;NO INTERRUPTS WHILE WE
          MOV XR2,AL                ;UPDATE THE RAM IMAGE
          OUT 2,AL                  ;AND THE REGISTER
          STI                       ;
;
;UNBLANK THE SCREEN IF APPROPRIATE
;
          CMP BLNK,1                ;ARE WE BLANKED?
          JE C_LPX                  ;JUMP IF SO - DON'T
                                    ;WANT TO UNBLANK
;
          CMP RG,1                  ;SAME WITH RED/GREEN
                                    ;LIGHT ON
          JE C_LPX                  ;
;
```

```
        CMP FIX,1                    ;SAME WITH FIXATE LIGHT
                                     ;ON
        JE C_LPX                     ;
;
;
;WE WANT TO UNBLANK THE SCREEN
;
;THE HAITEX GLASSES TAKE A WHILE TO ACTIVATE - TOGGLE LINES
;FOR TWO VERTICAL INTERVALS TO GET THEM GOING FIRST
;
;
        CALL V_WAIT                  ;WAIT FOR A VERTICAL
                                     ;INTERVAL
;
        CLI                          ;TOGGLE THE LINES
        MOV AL,XR2                   ;FETCH RAM IMAGE
        XOR AL,0C0H                  ;CHANGE BITS FOR BOTH
                                     ;EYES
        MOV XR2,AL                   ;UPDATE RAM IMAGE
        OUT 2,AL                     ;AND UPDATE REGISTER
        STI                          ;
;
        CALL V_WAIL                  ;WAIT FOR A VERTICAL
                                     ;INTERVAL
;
        CL1                          ;TOGGLE THE LINES
        MOV AL,X2                    ;
        XOR AL,0C0H                  ;
        MOV XR2,AL                   ;
        OUT 2,AL                     ;
        STI
        CALL V_WAIT                  ;WAIT FOR A VERTICAL
                                     ;INTERVAL
;
        CLI                          ;TOGGLE THE LINES
        MOV AL,XR2                   ;
        XOR AL,0C0H                  ;
        MOV XR2,AL                   ;
        OUT 2,AL                     ;
        STI                          ;
;
;GLASSES HAVE HAD TIME TO ACTIVATE
;
        MOV AL,XR5                   ;NOW UNBLANK THE SCREEN
        AND AL,0FEH                  ;CLEAR BLANKING BIT
        CLI                          ;UPDATE
        OUT 5,AL                     ;REGISTER
        MOV XR5,AL                   ;AND RAM IMAGE
        STI                          ;
;
;
;NOW TOGGLE THE INTERFACE LINES UNTIL A KEY IS PRESSED
;
C_LPX:  CALL V_WAIT                  ;WAIT FOR A VERTICAL
                                     ;INTERVAL
```

```
        CLI                    ;TOGGLE THE LINES
        MOV AL,XR2             ;FETCH RAM IMAGE
        XOR AL,0C0H            ;CHANGE BITS FOR BOTH
                               ;EYES
        MOV XR2,AL             ;UPDATE IMAGE
        OUT 2,AL               ;UPDATE REGISTER
        STI                    ;
;
        ADD TIMER,19           ;ADD 17 MSEC TO THE
        ADC TIMER+2,0          ;TIMER
;
;CHECK FOR A TIMEOUT - QUIT IF 10 MINUTES HAS GONE BY
;
        CMP TIMER+2,10         ;10 MINUTES UP?
        JAE C_C                ;QUIT IF SO
;
;CHECK FOR ANY KEYBOARD COMMANDS PENDING
;
        CMP KEY_BUF,0          ;NO COMMANDS PENDING?
        JNE C_C                ;JUMP IF COMMANDS
        CMP KEY_BUF_C,0        ;
        JNE C_C                ;
;
        CMP KEY_INT,1          ;WERE WE BLANKED BY A
                               ;KEYBOARD INTERRUPT?
        JE C_C                 ;EXIT IF SO
;
;
        JMP C_LPX              ;LOOP TILL COMMANDS
                               ;AVAILABLE
;
;
;TIME TO EXIT - BLANK THE GLASSES (WON'T WORK WITH HAITEX
;GLASSES DRIVER)
;
C_C:    MOV AL,XR2             ;FETCH RAM IMAGE OF
                               ;REGISTER
        OR AL,0C0H             ;SET BOTH BITS TO 'OFF'
        CLI                    ;
        MOV XR2,AL             ;UPDATE THE RAM IMAGE
        OUT 2,AL               ;AND THE REGISTER
        STI                    ;
;
CXXX:   POP CX                 ;RESTORE REGISERS USED
        POP AX                 ;
;
        RET                    ;
;
TOGGLE  ENDP                   ;
```

We claim:

1. A method for testing binocular vision using a display comprising the steps of:
   alternately displaying images on the display at a frequency sufficient to maintain fusion;
   alternately blocking or permitting a patient's viewing of the display; and
   synchronizing the displaying of the alternating images with blocking or permitting the patient's viewing such that some images are visible only to the patient's left eye, some images are visible only to the patient's right eye, and some images may be visible to both of the patient's eyes.

2. The method defined in claim 1 wherein the display is a video display monitor.

3. The method defined in claim 2 wherein the video display monitor uses a liquid crystal display.

4. The method defined in claim 2 wherein the video display monitor uses a raster scan cathode ray tube.

5. The method defined in claim 3 wherein the alternating images are presented on alternating interlaced screens of scan lines displayed on the monitor.

6. The method defined in claim 1 wherein the display of alternating images is achieved by means of alternating frames of a film.

7. A method of testing visual function to determine a patient's degree of stereo acuity comprising the steps of claim 1, and further comprising:
displaying at least one symbol such that it is displaced laterally to at least one eye than other symbols displayed.

8. The method of claim 7 wherein said predetermined pattern is diamond-shaped.

9. A method of testing visual function to evaluate ocular motor imbalance comprising the steps of claim 1, and further comprising:
displaying at least one target symbol to one eye of the patient and preventing the display of said target symbols to the second eye of the patient;
displaying a test symbol at a reference position to the second eye and preventing the display of the test symbol to the first eye; and
moving the test symbol away from said reference position in steps of predetermined distances until it appears to the patient that the test symbol is aligned with one of said other target symbols.

10. The method of claim 9, wherein said test symbol is moved horizontally, for evaluating horizontal ocular motor imbalance.

11. The method of claim 9, wherein said test symbol is moved vertically, for evaluating vertical ocular motor imbalance.

12. The method of claim 9, further comprising the step of displaying at least one visual target to both of the patient's eyes to provide a fixation lock for evaluating fixation disparity.

13. A method for detecting phoria comprising the steps of claim 1, and further comprising:
displaying two horizontal lines in the same horizontal plane, such that the first horizontal line is visible to one eye of the patient and the second horizontal line is visible to the second eye of the patient.
displaying two vertical lines in the same vertical plane, such that the first vertical line is visible to one eye of the patient and the second vertical line is visible to the second eye of the patient;
determining whether the vertical and horizontal lines appear to the patient to be in the same vertical and horizontal planes, respectively.

14. The method of claim 13, further comprising the step of displaying at least one visual target to both of the patient's eyes to provide a fixation lock for detecting associated phoria.

* * * * *

UNITED STATES PATENT AND TRADEMARK OFFICE
CERTIFICATE OF CORRECTION

PATENT NO. : 5,026,151
DATED : June 25, 1991
INVENTOR(S) : Morey H. Waltuck et al.

It is certified that error appears in the above-indentified patent and that said Letters Patent is hereby corrected as shown below:

On the cover page, under the heading References Cited, change "Blankehorn" to -- Blankenhorn --.

On the cover page, between the last cited U.S. patent (4,870,486) and the "Primary Examiner" entry, insert:

-- OTHER DOCUMENTS

B-VAT II Video Acuity Tester Instruction Manual, Mentor O & O, Inc., (1987).

"AO Custom Project-O-Chart Slides," Instruction Manual, AO American Optical. (date unknown)

"AO Vectographic Project-O-Chart Slides," product literature, AO American Optical. (date unknown)

"The TVA: True Visual Acuity," InnoMed Corp. product literature. (date unknown)

InnoMed Corp. product advertisement

Mentor O&O, Inc. B-VAT product literature (date unknown)

"B-VAT Video Acuity Tester Instruction Manual," Mentor O&O, Inc. (date unknown)

Stereo Optical Company, Inc. product literature (date unknown)

The TVA Operations Manual, Technical Enginuities Corp. (1985).

UNITED STATES PATENT AND TRADEMARK OFFICE
CERTIFICATE OF CORRECTION

PATENT NO. : 5,026,151  
DATED : June 25, 1991  
INVENTOR(S) : Morey H. Waltuck et al.

Page 2 of 3

It is certified that error appears in the above-indentified patent and that said Letters Patent is hereby corrected as shown below:

"TVA Revolutionizing Refracting," InnoMed Corp. product literature, (1985).

Fahle, M. and Erb, M., "Presenting Stereoscopic Stimuli With One Monitor," Vision Research, Vol. 27, No. 8, pp. 1391-92 (1987)

Lindblom, B. and Frisen, L., "Measuring Stereo Acuity with Liquid Crystal Shutters and Computer Graphics," Neuro-ophthalmology, Vol. 8, No. 6, pp. 283-87 (1988)

Handaya Co., Ltd. product literature, New Aniseikonia Tests (date unknown)

Duane, Clinical Ophthalmology, Vol. 1, Ch. 9, pp. 8-11 (date unknown)

Fahle, M. and Westheimer, G., "Local and Global Factors in Disparity Detection of Rows of Points," Vision Research, Vol. 28, No. 1, pp. 171-78 (1988) --

At column 2, line 35, change "flexiblity" to -- flexibility --.

At column 3, line 15, change "electrooptical" to -- electro-optical --.

At column 8, line 49, delete -- and --.

UNITED STATES PATENT AND TRADEMARK OFFICE
CERTIFICATE OF CORRECTION

PATENT NO. : 5,026,151
DATED : June 25, 1991
INVENTOR(S) : Morey H. Waltuck et al.

It is certified that error appears in the above-indentified patent and that said Letters Patent is hereby corrected as shown below:

At column 22, line 7, change "IS" to -- IF --.

At columns 23-24, line 4, change "VETICAL" to -- VERTICAL --.

At column 24, line 35. change "CONROLS" TO -- CONTROLS --.

At column 25, line 24, change "V__WAIL" to -- V__WAIT --.

At column 28, line 44, change "REGISERS" to -- REGISTERS --.

Signed and Sealed this

Twenty-first Day of June, 1994

BRUCE LEHMAN

Attest:

Attesting Officer

Commissioner of Patents and Trademarks